(12) United States Patent
Ahn et al.

(10) Patent No.: US 7,629,744 B2
(45) Date of Patent: Dec. 8, 2009

(54) IN-GEL TAGGING AND IN-GEL DIGESTION FOR PHOSPHOPROTEINS ANALYSIS AND PHOSPHORYLATION SITE IDENTIFICATION

(75) Inventors: Yeong Hee Ahn, Chungcheongbuk-do (KR); Jong Shin Yoo, Daejeon-shi (KR); Jae Yong Lee, Daejeon-shi (KR); Jin Young Kim, Daejeon-shi (KR); Kun Cho, Daejeon-shi (KR)

(73) Assignee: Korea Basic Science Institute, Daejeon-Shi (KR)

( * ) Notice: Subject to any disclaimer, the term of this patent is extended or adjusted under 35 U.S.C. 154(b) by 172 days.

(21) Appl. No.: 11/574,660

(22) PCT Filed: Oct. 8, 2004

(86) PCT No.: PCT/KR2004/002577

§ 371 (c)(1),
(2), (4) Date: Mar. 2, 2007

(87) PCT Pub. No.: WO2006/028310

PCT Pub. Date: Mar. 16, 2006

(65) Prior Publication Data

US 2007/0287169 A1  Dec. 13, 2007

(30) Foreign Application Priority Data

Sep. 4, 2004  (KR) ............... 10-2004-0070651

(51) Int. Cl.
*H01J 17/26* (2006.01)
(52) U.S. Cl. .................................... 313/564
(58) Field of Classification Search .............. None
See application file for complete search history.

(56) References Cited

FOREIGN PATENT DOCUMENTS

KR  1020050079558  8/2005

OTHER PUBLICATIONS

Oda et al. "Enrichment analysis of phosphorylated proteins as a tool for probing the phosphoproteome", Nature Biotechnology, 2001, 19:379-382.*
Stensballe et al. "Simplified sample preparation method for protein identification by matrix-assisted laser desorption-ionization mass spectrometry: in-gel digestion on the probe surface", Proteomics, 2001, 1:955-966.*

* cited by examiner

*Primary Examiner*—Karen Cochrane Carlson
*Assistant Examiner*—Bin Shen
(74) *Attorney, Agent, or Firm*—Lucas & Mercanti, LLP

(57) ABSTRACT

The present invention relates to a method for phosphorylation site-specific labeling of phosphoproteome with a site-specific tagging reagent and analyzing of the resulting labeled one, more especially, a method for in-situ tagging of phosphorylation sites of phosphoproteins retained in polymeric gel with a nucleophilic tagging reagent. It also relates a method for generating new proteolytic cleavable sites at formerly phosphorylation sites by a proper choice of a nucleophilic tagging reagent. It also relates to a method for phosphopeptides analysis and phosphorylation site identification by in-gel digestion of the previously in-gel tagged proteins and subsequent mass analysis of the resulting peptides. The invention provides in-gel chemical tagging method for phosphoaminoacid residue of phosphoproteins retained in polymeric gel matrix. Phosphoprotein can be immobilized into gel matrix by a variety of methods such as gel electrophoresis. The immobilized phosphoproteins are retained in gel matrix during tagging reaction to phosphorylated aminoacid residue of phosphoproteins, and the resulting tagged proteins are also retained in gel matrix till following purification steps like washing of the tagging reagents are accomplished. The tagged proteins is digested by protease, and the resulting digested peptides is released from gel into solution and applied for peptide mass analysis.

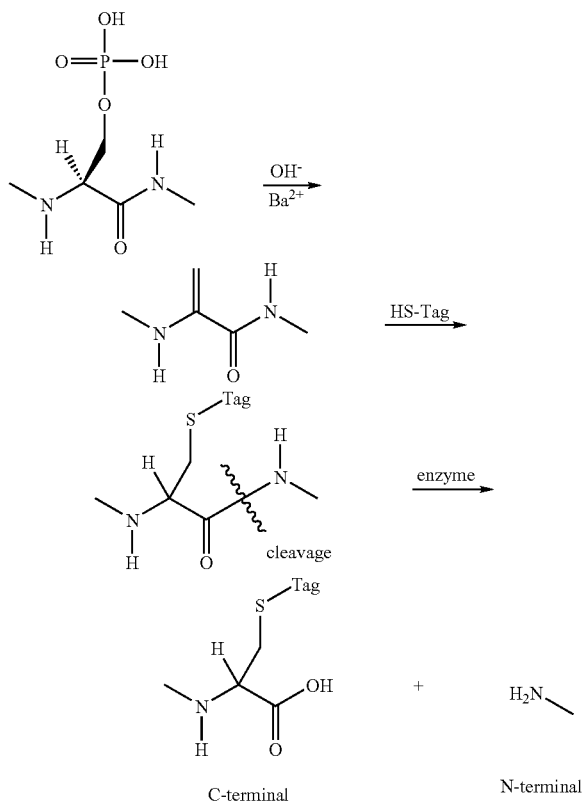

23 Claims, 4 Drawing Sheets

[Fig. 1]
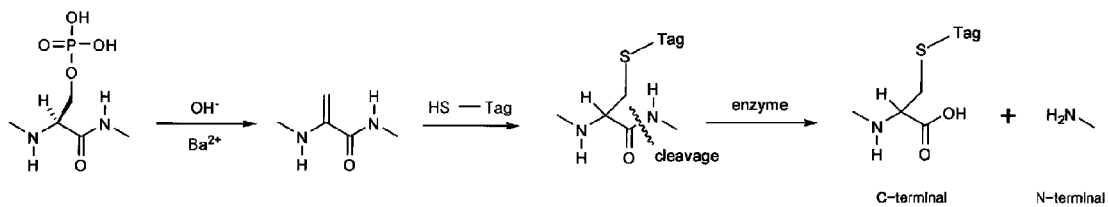
[Fig. 2]
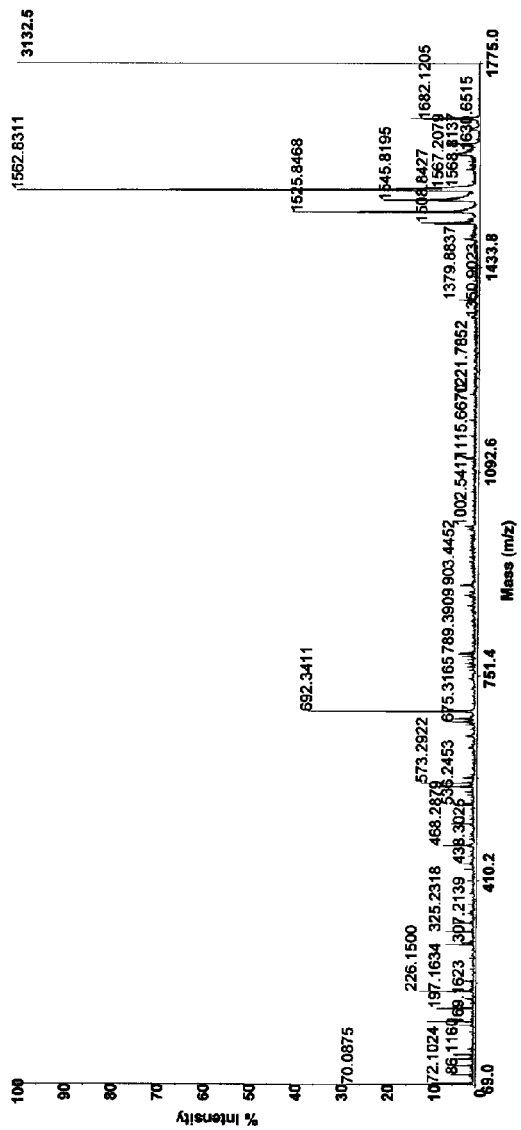

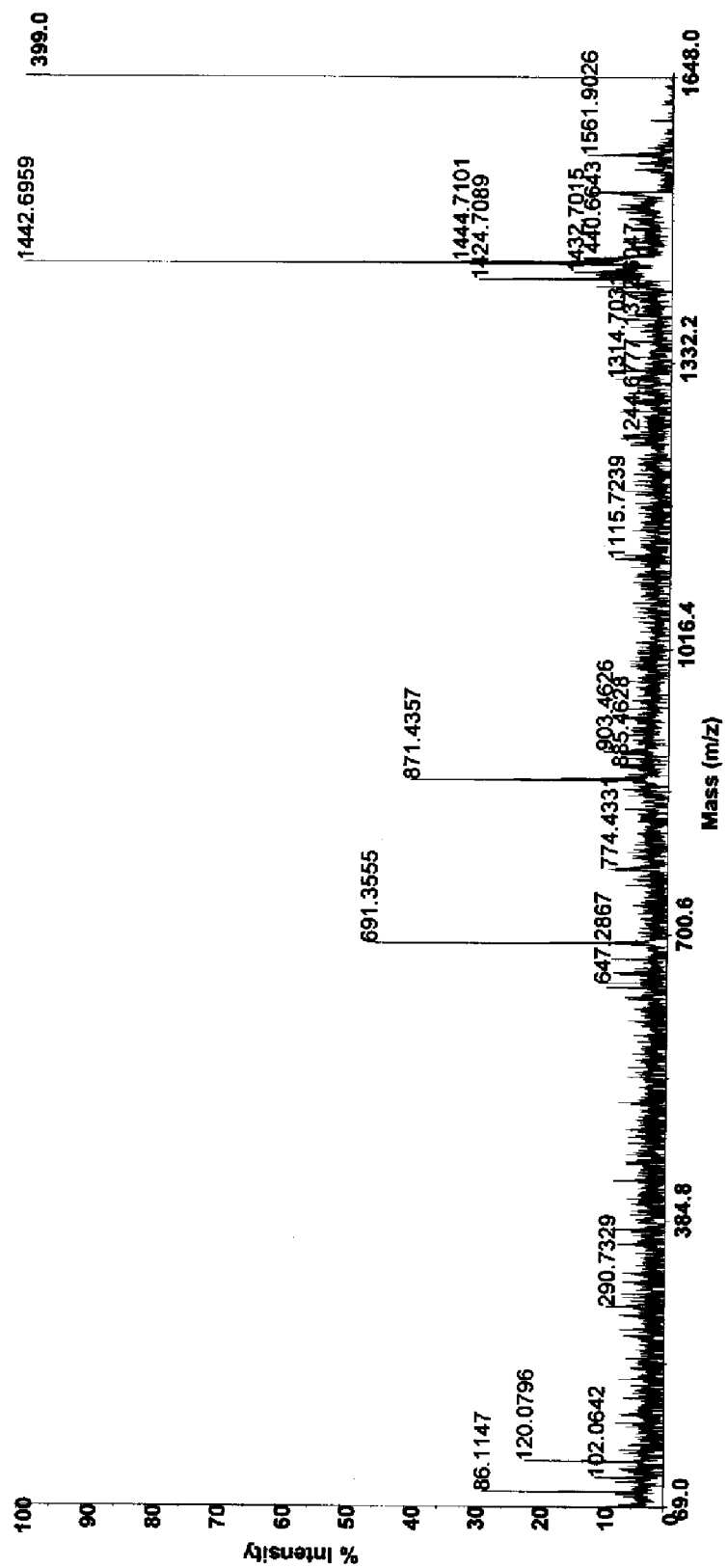
[Fig. 3]

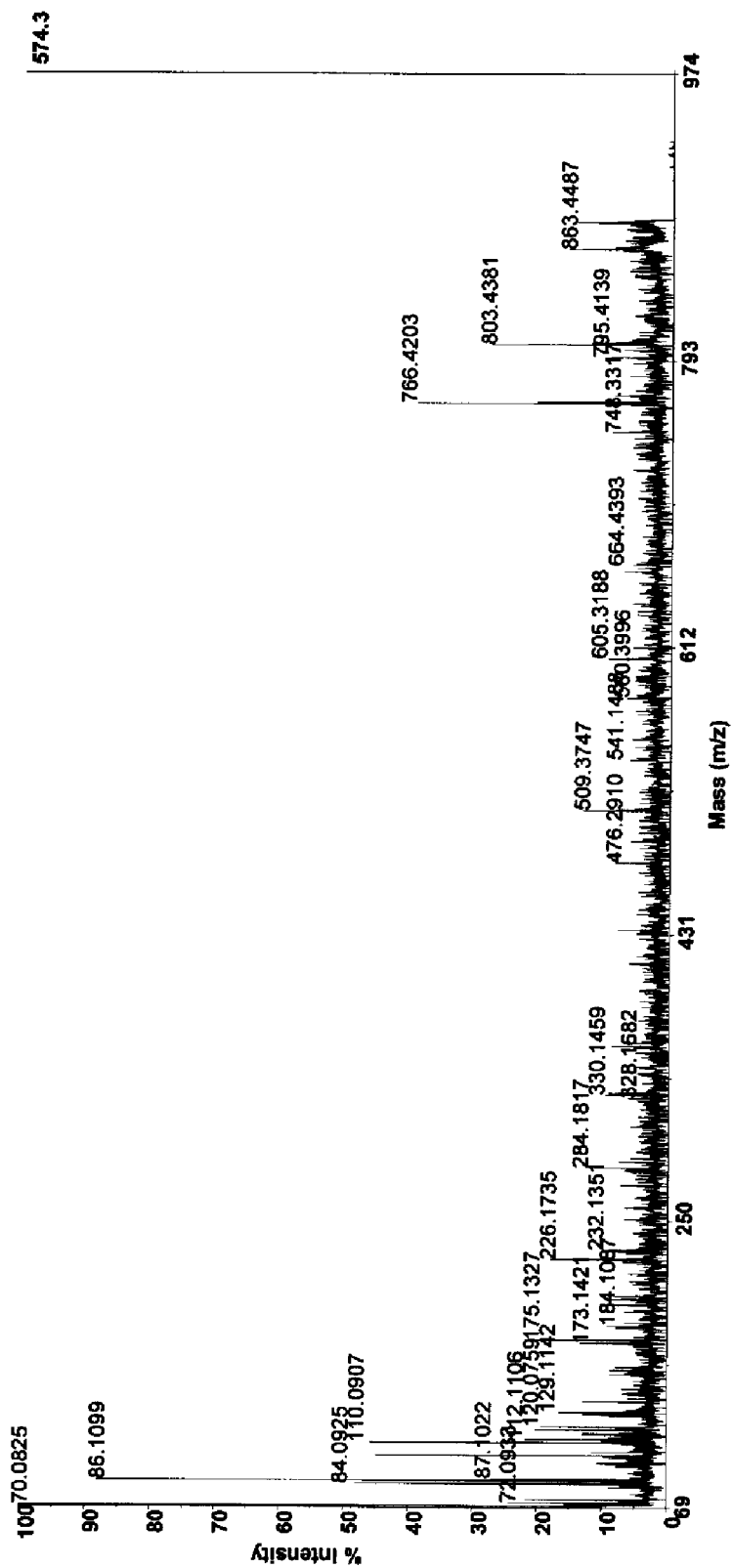
[Fig. 4]

[Fig. 5]
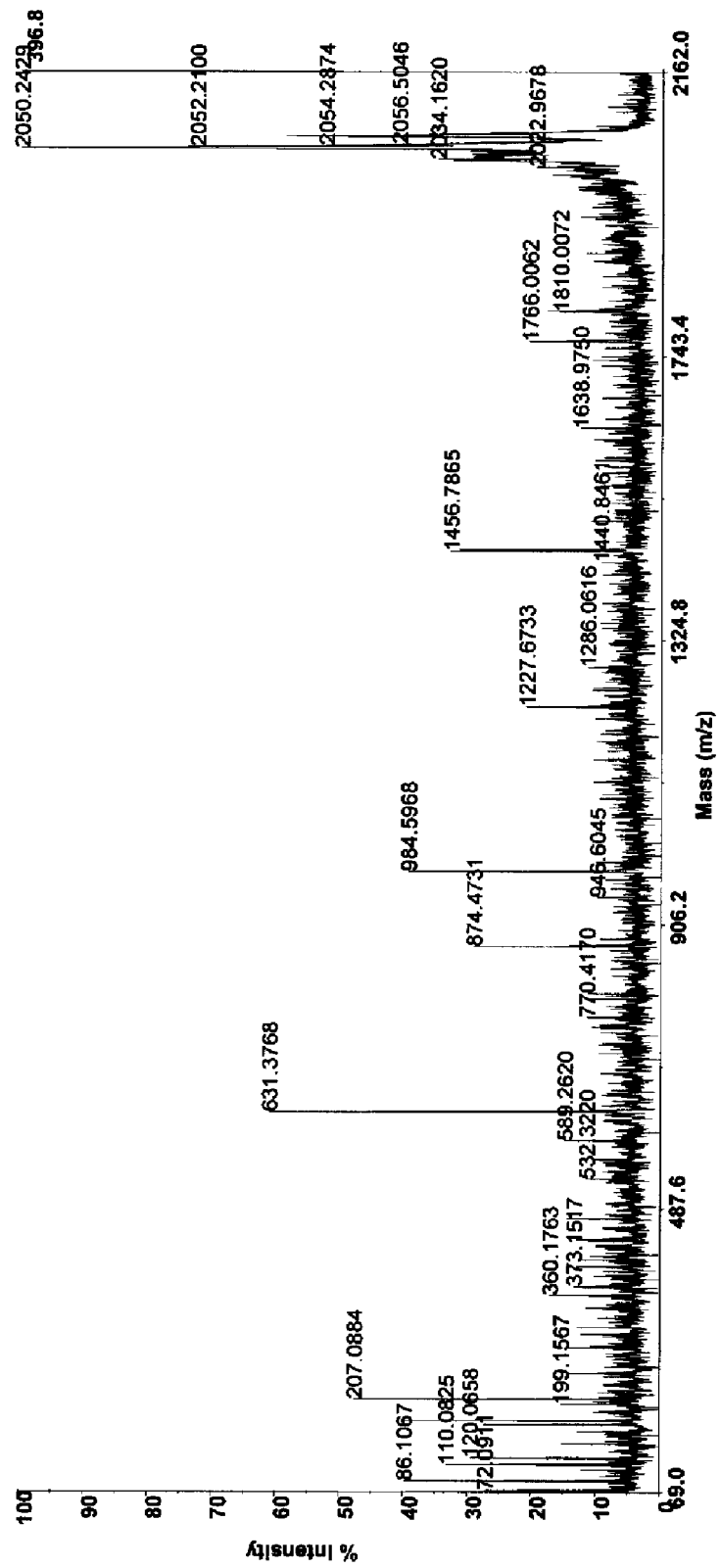

IN-GEL TAGGING AND IN-GEL DIGESTION FOR PHOSPHOPROTEINS ANALYSIS AND PHOSPHORYLATION SITE IDENTIFICATION

CROSS-REFERENCE TO RELATED APPLICATION

This application is a 371 of PCT/KR2004/002577 filed on Oct. 8, 2004, which claims the benefit of Korean Patent Application No. 10-2004-0070651 filed on Sep. 4, 2004, the contents of each of which are incorporated herein by reference.

TECHNICAL FIELD

The present invention relates to a method for phosphorylation site-specific labeling of phosphoproteome with a site-specific tagging reagent and analyzing of the resulting labeled one, more especially, a method for in-situ tagging of phosphorylation sites of phosphoproteins retained in polymeric gel with a nucleophilic tagging reagent. It also relates a method for generating new proteolytic cleavable sites at formerly phosphorylation sites by a proper choice of a nucleophilic tagging reagent. It also relates to a method for phosphopeptides analysis and phosphorylation site identification by in-gel digestion of the previously in-gel tagged proteins and subsequent mass analysis of the resulting peptides.

BACKGROUND ART

Phosphorylation of proteins, one of the most impotent post translational modification (PTM), play impotent roles to control many cellular processes in signal transduction, gene expression, apoptosis. Therefore considerable effort has been devoted to developing methods to detect the phosphoprotein and quantify the phosphorylation states of the protein. In general, phosphorylation of protein, one of post-translational modifications of protein in biological medium, is observed in aminoacid residue such as serine, threonine, histidine, and lysine. Phosphorylation is reversible process, mainly controlled by protein kinase for phosphorylation and by phosphatase for dephosphorylation.

It is widely recognized that irregularity of protein phosphorylation states, such as abnormal phosphorylation or dephosphorylation, relates to nanny diseases. Thus the development of efficient diagnostic method for irregularity of phosphorylation states is very urgent and impotent in the understanding of a variety of biological states relevant to diseases and will contribute to study for diagnose and treatment of diseases.

Mass spectrometry has become an increasingly viable, powerful alternative to old traditional methods for phosphorylation analysis. Nevertheless, analysis of phosphorprotein and phosphopeptide presents great challenges to be solved in mass spectrometry. First, phosphoprotein is often present in substoichiometric amount as a result of partial post-translational modification, and the phosphopeptides digested are present in lower abundance than the other unphosphorylated counterparts in the sample mixture. Second, negatively charged modification, as in phosphoprotein, may be less proteolytic activity by trypsin, and the regions of interest can be missed consequently in mass analysis. Third, the ionization of negatively charged phosphopeptides in a positive mode are also suppressed relative to other unphosphorylated peptides, and the suppression effect is especially increased according to increase of complexity of the peptide mixture. Forth, the partial dephosphorylation of phosphate group from phosphopeptide during mass analysis can be occurred by virtue of chemical instability of phosphate linkage. It can result in decrease of mass sensitivity and increase of complexity of mass spectrum, and become cause of incomplete peptide sequence in mass/mass (MS/MS) sequencing.

For purification, enrichment and high-sensitive mass analysis of phosphopeptides digested from phosphoproteins, several analytical tools were developed such as antibody affinity enrichment, immobilized metal affinity chromatography (IMAC) enrichment, and chemical tagging methods of phosphorylation sites. Among above methods, chemical tagging methods of phosphorylation sites are a efficient analytical tool for phosphoproteome analysis, especially in proteomic field using mass spectrometry. Some chemical tagging methods, based on the b-elimination of phosphor serine (or phosphorthreonine) to generate dehydroalanine (or b-methyldehydroalanine) under basic conditions and the conjugate addition of highly nucleophilic tagging reagent to the resulting conjugate peptides, have been reported for enrichment, MS/MS sequence and relative quantitation of phosphorpeptides digested from phosphorproteins. Reagents having sulfhydryl functionality, such as mercaptoethanol, mercaptoethylamine, ethanedithiol etc., is usually selected as a nucleophile for tagging reaction. The chemical tagging methods especially have merit for high sensitive detection of phosphopeptides, because of the replacement of phosphate group with chemical tag having a high proton affinity increase the ionizability of peptide moiety originally phosphorylated. This chemically tagged peptide is now unsuppressed in mass analysis, and will show greatly increased detectability comparable to that in originally unphosphorylated peptides, even in complex peptide mixture. Additionally the mass shift in spectra due to dephosphorylation (−98 Da) and attachment of chemical tag will help to identify phosphopeptides in complex mass spectra and to assign the sites of phosphorylation in phosphorpeptides.

For high sensitive detection and easy assignment of phosphopeptides from tryptic digest peptides mixture of phosphoprotein, we developed a new β-elimination/chemical tagging method using tag reagent containing guanidine moiety. Guanidination of C-terminal lysine residue of tryptic peptide mixture to hanoarginine residue using O-methyl isourea was reported to increase the mass sensitivity of the modified peptides in positive ion made mass analysis. Gianidino group is actually more basic than that of primary amino group. Gianidinoethanethiol (GET) having both guanidine moiety and high nucleophilic sulfhydryl moiety has a proper structure as a tagging reagent for tagging of phosphorylation sites in phosphorpeptides and phosphoproteins. GET is generated from commercially available (lanidinoethyl disulfide (GEDS) by a proper reducing reagent and compatible with aqueous condition for tagging reaction of phosphorpeptides and phosphorproteins.

On the other hand, the chemical tagging method for phosphoproteins can be carried out in phosphoprotein level before enzymatic digestion of phosphoproteins. A variety of chemical tags are developed and applied to tag phosphoproteins. Enzymatic digestion for protein chemically tagged at the sites formerly phosphorylated is affected from the tag moieties in its enzymatic selectivity. Knight, Z. A. et. al.(Nature Biotechnology, Vol. 21, No. 9, p. 1047, September 2003) use aminoethanethiol as a tagging reagent to phosphorylated sites of phosphoprotein. Aminoethylcysteine residue produced from tagging of aminoethanethiol to formerly phosphoserine residue is play like lysine residue in enzymatic digestion using protease such as trypsin. Thus tagging to phosphoprotein using chemical tag inducing phosphospecific proteolysis can be a powerful tool for assigning of phosphorylated sites in phosphoprotein. Peptides resulting from phosphospecific proteolysis will give $y_1$ fragment ion corresponding to aminoethylcysteine fragment in MS/MS peptide sequence analysis. Korea patent application No. 2004-0008046 discloses selective labeling agent for phosphoproteome analysis and phosphorylated site analysis.

DISCLOSURE OF INVENTION

The invention provides in-gel chemical tagging method for phosphoaminoacid residue of phosphoproteins retained in polymeric gel matrix. Phosphoprotein can be immobilized into gel matrix by a variety of methods such as gel electrophoresis. The immobilized phosphoproteins are retained in gel matrix during tagging reaction to phosphorylated aminoacid residue of phosphoproteins, and the resulting tagged proteins are also retained in gel matrix till following purification steps like washing of the tagging reagents are accomplished. The tagged proteins is digested by protease, and the resulting digested peptides is released from gel into solution and applied for peptide mass analysis.

The invention also provides phosphospecific proteolysis method to enable proteolysis at the tagged aminoacid residue generated as a result of in-gel chemical tagging reaction to phosphorylated aminoacid residue with site-specific tagging reagents. In the phosphospecific proteolysis method, the site-specific tagging reagent is tagged firstly at α,β-unsaturated aminoacid residue resulting from β-elimination of phosphate group in phosphorylated aminoacid residue of phosphoproteins retained in polymeric gel matrix. And the tagged aminoacid residue has a similar structural feature to be recognizable as an enzymatic cleavable site by protease such as trypsin. For example, guanidinoethylcysteine, derivatized from phosphoserine by the phosphospecific chemical tagging reaction, is resemble homoarginine and recognized to be digested site by protease. Thus in-gel digestion for phosphoproteins modified by enzyme-recognizable chemical tag gives peptides mixture including modified peptides resulting from peptide bond cleavage of formerly phosphorylated site.

Mass analysis of peptides, obtained from the in-gel chemical tagging for phosphoproteome retained in polymeric gel matrix and the subsequent in-gel digestion of the resulting chemically tagged proteome, provides lots of information for phosphorylation state of sample protein. The unique mass shift due to the chemical tagging reaction at formerly phosphorylated site gives impotent information for the site of phosphorylation in MSIMNS analysis. Enzymatic peptide bond cleavage at the chemically tagged aminoacid residue, formerly phosphorylated, provides peptides having the tagged aminoacid residue as C-terminal.

BRIEF DESCRIPTION OF THE DRAWINGS

The preferred embodiments of the present invention is best understood with reference to the accompanying drawings, wherein:

FIG. 1 is phosphospecific labeling with guanidinoethanethiol and subsequent proteolysis of the tagged site, FIG. 2 is MS/MS spectrum of the peptide (sequence VPQLEIVPNS*AEER, m/z 1682, SEQ ID NO:1)of α-casein, which is in-gel tagged phosphospecifically with guanidinoethanethiol, and in-gel digested subsequently. S* denotes guanidinoethylcysteine site, formerly phosphoserine site, FIG. 3 is MS/MS spectrum of the peptide (sequence S*EEI VPNS*VEQK, m/z 1561, SEQ ID NO:2) of α-casein, which is in-gel tagged phosphospecifically with guanidinoethanethiol, and in-gel digested subsequently. S* denotes guanidinoethylcysteine site, formerly phosphoserine site, FIG. 4 is MS/MS spectrum of the peptide (sequence S*EESITR, m/z 922,SEQ ID NO:3) of β-casein, which is in-gel tagged phosphospecifically with guanidinoethanethiol, and in-gel digested subsequently. S* denotes guanidinoethylcysteine site, formerly phosphoserine site, FIG. 5 is MS/MS spectrum of the peptide (sequence GFS-GEDAT-PALEGADVVLIS*, m/z 2049, SEQ ID NO:4) of malate dehydrogenase[*Escherichia coli*], which is in-gel tagged phosphospecifically with guanidinoethanethiol, and in-gel digested subsequently. S* denotes guanidinoethylcysteine site, formerly phosphoserine site.

BEST MODE FOR CARRYING OUT THE INVENTION

The invention comprises following steps;

1)dephosphorylation of phosphate groups from phosphoproteins immobilized in polymeric gel matrix, and in-gel conjugate addition to the resulting dephosphorylated aminoacid residues by a nucleophilic chemical tag, 2)selective remove of reagents used for the in-gel chemical tagging reaction of phosphoproteins from polymeric gel matrix, 3)in-gel digestion of phosphospecific tagged proteins retained in polymeric gel to afford digested peptide mixture, consisting of nonphosphopeptides and chemically tagged peptides with or without enzymatic cleavage at tagged amino acid residue, formerly phosphorylated, 4)and chromtographic purification and mass analysis for the digested peptides released from polymeric gel matrix.

In the invention, phosphoproteins mentioned in the above step 1) can be prepared from a variety of cell membrane, different organelles, subcellular tissues following conventional method using in related field. Phosphoproteins can also selected from proteins, expressed in different disease states, expressed in response to different environmental or nutritional conditions, different physical or chemical stresses, or at different times. The phosphoproteins prepared through a conventional methods such as denaturation, reduction, cysteine alkylation, deglycosylation etc. can be immobilized into polymeric gel matrix following a conventional methods using in gel electrophoresis field. Gel having a variety of gel density can be used following a necessity.

The immobilized proteins can also be separated by widely used 1D or 2D gel electrophoresis method, if necessary. It is well known that mn)st of phosphoproteins once immobilized into gel matrix is retained in gel and not released into solution being used through a variety of treatment steps such as staining, destaining, cysteine alkylation, etc. Thus the gel matrix can play like a vessel containing samples, phosphoproteins.

Following the invention, the ability of gel matrix to immobilize protein also can be employed as a reaction vessel for phosphospecific chemical tagging reaction of phosphoproteins retained in gel. Stained gel slices retaining phosphoproteins, prepared with a proper size, is destained and washed by a conventional method for following chemical tagging step. β-Elimination/Michael addition method is widely used in solution phase for selective labeling of phosphorylated sites of phosphoproteome. β-Elimination step is represented by the following reaction formula 1

<Reaction Formula 1>

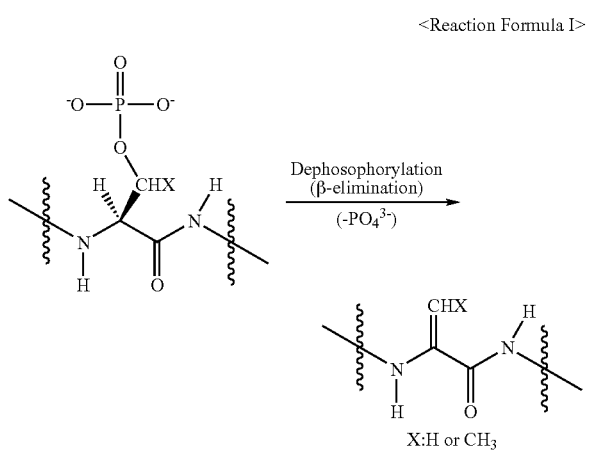

X:H or CH₃

In the reaction formula 1, the amino acid residue is phosphoserine for X=H and phosphothreonine for X=CH₃.

Dephosphorylation, β-elimination, of phosphate groups from phosphoproteins immobilized in polymeric gel matrix was carried under basic aqueous tagging solution containing a metal catalyst, selected from cations of elements belong group II in periodic table such as $Mg^{2+}$, $Ca^{2+}$, $Sr^{2+}$ or $Ba^{2+}$. As a result of dephosphorylation of phosphate groups from phosphoproteins, phosphoserine residues and/or phosphothreonine residues presenting in phosphoproteins are converted to dehydroalanine residues and/or β-methyldehydroalanine residues respectively. The resulting dephosphorylated aminoacid residue having α,β-unsaturated conjugate system play as a good acceptor for sulfilydryl nucleophile presenting in the tagging solution. Thus through Michael addition of a proper chemical tag to dephosphorylated sites of proteins being immobilized into gel matrix, formerly phosphorylated sites of phosphoproteins in mobilized are converted to sites tagged with the tag. Michael addition reaction is represented by the following reaction formula 2.

<Reaction Formula 2>

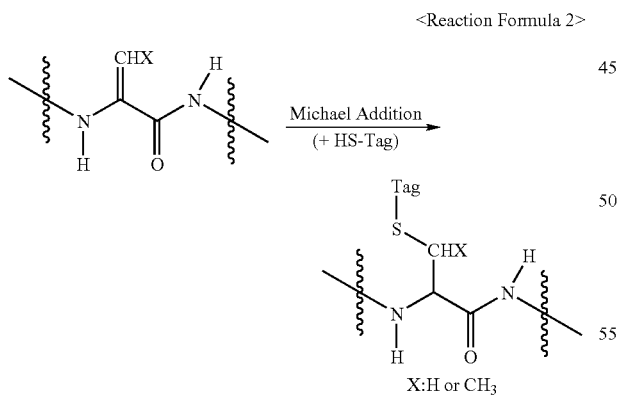

X:H or CH₃

In the reaction formula 2, the amino acid residue is dehydroalanine for X=H and β-methyldehydroalanine for X=CH₃, which had been generated respectively from phosphoserine and phosphothreonine by β-elimination.

Tag compound in the invention can be selected from group consisting of compounds having strong nucleophilicity to α,β-unsaturated conjugate system generated from β-elimination of phosphate group. The reagent having thiol functionality is preferable. The thiol group can also be prepared in situ or in advance tagging reaction from its precursor form like disulfide, and thio ester etc. The tagging reagent can also be selected from group consisting of compounds capable of affording similar structural features with lysine or arginine from its conjugate addition to dephosphorylated aminoacid residue, and playing as a lysine or arginine mimic during enzymatic hydrolysis, resulting peptide bond cleavage at the tagged sites, formerly phosphorylated sites, by enzymatic digestion. Thus chemically tagged sites to resemble lysine or arginine, which is formerly phosphorylated, are hydrolyzed by protease such as trypsin, and corresponding to C-terminal aminoacid residue in resulting peptides. Knight, Z. A. et. al., reported that aminoethylcysteine can be used as a chemical tag to afford a lysine mimics to be recognized and hydrolyzed by trypsin. It was also reported by Ahn, Y. H. et. al. that Guanidinoethylcysteine, homoarginine mimics, can play like a arginine, and be hydrolyzed by trypsin. As an example of the invention, phosphoaminoacid residues of phosphoprotein immobilized in polymeric gel were converted to guanidinoethylcysteine residues or β-methylguanidinoethylcysteine residues by the in-gel chemical tagging method mentioned above, in which guanidinoethanethiol, in-situ generated from guanidinoethanedisulfide by reducing reagent, is used as a chemical tag. After all reagents used during tagging reaction were washed from polymeric gel matrix, the phosphospecific tagged protein being in gel matrix was in-gel digested to afford peptide mixture containing peptides cleaved at the tagged aminoacid residue, formerly phosphorylated aminoacid residue. Proteolysis at the guanidinoethylcysteine residue, formerly phosphorserine residue, is represented by the following reaction formula 3.

<Reaction Formula 3>

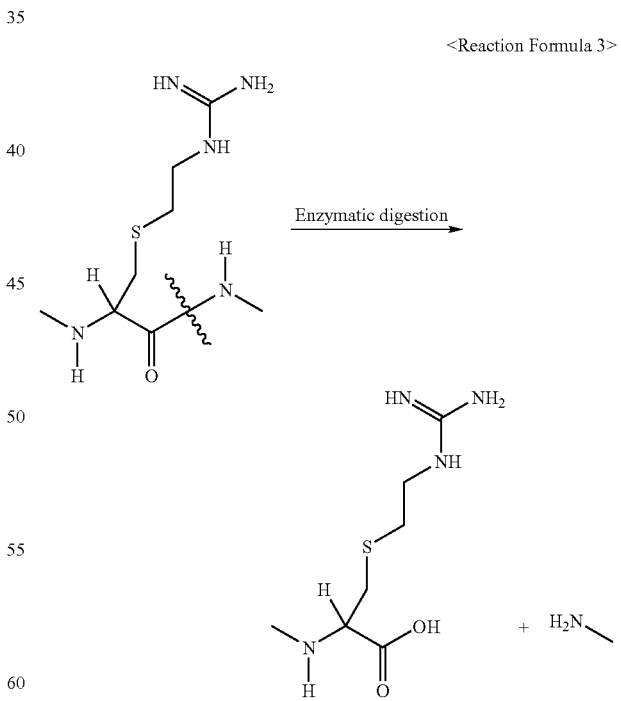

The in-gel tagging reaction can be carried separately or coincidently with the dephosphorylation reaction of phosphoprotein. The nucleophile can also be generated from its precursor form in advance or coincidently with the tagging reaction. The relative quantification for phosphorylation state between samples obtained different sources is also possible as a stable isotope-coded tag is used for sample tagging differentially.

For example, guanidinoethanol and its isomer isotopically coded with isotope of each consisting atom such as hydrogen, carbon, nitrogen and sulfur atom are same each other in chemical structure, chemical properties, and reactivity and the like except for molecular weight that exhibit constant mass difference. Therefore, in in-gel tagging reaction and subsequent in-gel digestion, the above guanidinoethanol and its isomer exhibit the sane reactivity and properties, but a difference for mass of the isomer tagged at each peptide is exhibited on mass spectrum at the only mass analysis for the tagged peptides. Therefore, it can be analyzed for the relative quantity between two tagged peptides that are presence each in two samples from the intensity of their mass spectrum due to two peptides which have the sane amino acid sequence but exhibit mass difference corresponding to the difference of mass number for two isomer used as tagging agent. Gishe, M. B. et, al published such relative quantifying method using another specific tagging agent(US 2002/0119505), it can be applied the present invention.

Reagents of high concentration were used for the in-gel tagging of phosphoproteins retaining in polymeric gel matrix. These reagents should be removed selectively from the gel for subsequent in-gel digestion of chemically tagged proteins. Thus during in-gel tagging reaction and several washing steps, polymeric gel matrix play like a vessel retaining protein sample. Washing of reagents used for tagging reaction was easily done by standing the gel in a proper composition of solvents selected from water and organic solvent, such as acetonitrile, methanol, ethanol, isopropanol etc. For adjust of pH of the washing solvent, addition of proper acid, base and/or buffer salts is also desirable. Acidic washing solvent is notably preferable for effective remove of tag reagent having a basic functionality. After washing the gel, the gel can be squeezed by standing in acetonitrile and dried in vacuum.

In-gel digestion was carried for protein tagged by the in-gel β-elimination/Micheal addition mentioned above. Like conventional methods used widely in the field, a variety of protease can be used for in-gel digestion of phosphospecifically tagged protein. Especially in case of in-gel tagging of phosphoprotein by a chemical tag capable of leading the phosphospecific proteolysis at the chemically tagged site like above mentioned, careful choice of protease is desirable for more selective digestion. For example, guanidinoethanethiol among several chemical tags converts phosphoaminoacid residue to guanidinoethylcysteine residue by the in-gel tagging method. The resulting guanidinoethylcysteine residue resembles structurally homoarginine. Thus the residue can be recognized and hydrolyzed selectively by arginine specific protease such as Endoproteinase Arg-C as well as widely using protease such as trypsin. On the other hand aminoethanethiol converts phosphoaminoacid residue to aminoethylcysteine residue by the in-gel tagging method. The resulting aminoethylcysteine residue resembles structurally lysine. Thus the residue can also be recognized and hydrolyzed selectively by lysine specific protease such as Endoproteinase Lys-C as well as widely using protease such as trypsin. Chance to choose of protease following the tag used in-gel tagging reaction can be an additional merit of the phosphospecific in-gel tagging/digestion method.

Released peptides from the gel are analyzed by a variety of peptide analytical tools with or without proper chromatographic pretreatments. The phosphospecific proteolysis, enzymatic cleavage of the tagged aminoacid residue formerly phosphorylated, gives a powerful tool for assigning phosphorylated sites in the phosphoprotein. Peptides resulting from phosphospecific proteolysis have the phosphospecific tagged residue (e.g. guanidinoethylcysteine, aminoethylcysteine etc.) as a C-terminal aminoacid residue, and give $y_1$ fragment ion corresponding to the tagged residue in MS/MS peptide sequence analysis. Even in case of occurrence of miss cleavage at the tagged sites in enzyme digestion, the phosphospecific tagged sites can be assigned from the occurrence of unique mass difference due to the tagged aminoacid residue fragment in MS/MS sequencing. It is also additional merit that mass sensitivity of phosphospecific tagged peptides is increased by virtue of remove of phosphate group in phosphopeptides.

FIG. 2 shows the MS/MS spectrum of GET-tagged peptide (sequence VPQLEIVPNS*AEER, m/z 1682, SEQ ID NO:1) of α-casein, which is in-gel tagged phosphospecifically with guanidinoethanethiol, and in-gel digested subsequently with trypsin. S* denotes guanidinoethylcysteine site, formerly phosphoserine site. Peak showing at m/z 1562.8 is due to the peptide fragment occurring as a result of neutral loss of guanidinoethanethiol from the precursor peptide. Peak showing at m/z 692.3 corresponds the y5 fragment ion resulting from the cleavage of peptide bond locating N-terminal of guanidinoethylcysteine, formerly phosphoserine site.

FIG. 3 shows MS/MS spectrum of the peptide (sequence S*EEIVPNS*VEQK, m/z 1561, SEQ ID NO:2) of α-casein, which is in-gel tagged, and in-gel digested subsequently. S* denotes guanidinoethylcysteine site, formerly phosphoserine site. Peaks (y5 and b7) corresponding fragment ions due to the cleavage of peptide band locating N-terminal of guanidinoethylcysteine, formerly phosphoserine site, appear at m/z 691.3 and 871.4 with relatively strong peak intensity. Thus phosphorylation site is easily and evidently identified.

FIG. 4 shows MS/MS spectrum of the peptide (sequence S*EESITR, m/z 922, SEQ ID NO:3) of β-casein, which is in-gel tagged, and in-gel digested subsequently. S* denotes guanidinoethylcysteine site, formerly phosphoserine site. The results show generality and applicability of the method, in-gel tagging/in-gel digestion method, for effective phosphoproteins analysis and phosphorylation site identification.

FIG. 5 shows MS/MS spectrum of the peptide (sequence GFSGEDAT-PALEGADVVLIS*, m/z 2049, SEQ ID NO:4) of malate dehydrogenase[*Escherichia coli*], which is in-gel tagged phosphospecifically with guanidinoethanethiol, and in-gel digested subsequently. S* denotes guanidinoethylcysteine site, formerly phosphoserine site. The peptide has the sequence that GET-tagged site, S*, locates at C-terminal residue as the result of enzymatic cleavage at the tagged aminoacid residue, guanidinoethylcysteine. Thus the MS/MS spectrum of the peptide shows a unique peak at m/z 207.1 corresponding y1 fragment ion of the peptide.

Practical and presently preferred embodiments of the present invention are illustrative as shown in the following Examples.

However, it will be appreciated that those skilled in the art, on consideration of this disclosure, may make modifications and improvements within the spirit and scope of the present invention.

MODE FOR THE INVENTION

EXAMPLE 1

Preparation of Sample Immobilized in Gel Matrix

Protein samples are extracted and prepared following a conventional method from a biological medium. The extracted proteins are denaturized with 6 M guanidine hydrochloride. Disulfide bonds of cysteine residue are reduced with tris(2-carboxyethyl)phosphine hydrochloride for about 1 h at about 37° C., and the formed thiol groups are blocked to carbanidanethyl with iodoacetaride or oxidized to sulfonic acid with performic acid following a known procedures. The prepared proteins can be separated and immobilized into polyacrylamide gel matrix following a conventional methods using in gel electrophoresis field. Polyacrylamide gel can be prepared from solutions having a variety of acrylamide concentration following a necessity. The proteins onto polyacrylamide gel can be separated by widely used 1D or 2D gel electrophoresis method, if necessary. The protein spots separated in gels are visualized by staining with silver nitrate or Coomassie Brilliant Blue G-250 by conventional methods.

EXAMPLE 2

In-gel tagging of immobilized phosphoproteins

The stained protein spots are excised from the gel, and destained with 30 mM potassium ferricyanide and 100 mM sodiumthiosulfate for gel stained with silver nitrate or with ammonium bicarbonate solution containing methanol or actonitrile for gel stained with Coomassie Blue. The gel destained is washed with acetonitrile and dried in vacuum.

Tagging solution is prepared by reduction of guanidinoethanedisulfide hydrochloride (GEDS 2HCl) with tris (2-carboxyethyl) phosphine hydrochloride (TCEP, neutralized). 0.5 M TCEP(20 μl) is mixed with 0.5M GEDS 2HCl(20 μl) under argon atmosphere. After water (2 μl) added, the reaction tube is standing for about 30 min. at about 45° C. without shaking. 5.0 N NaOH (6 μl) and 1.0 M $BaCl_2$ (2 μl) are added to the reaction tube consecutively. The prepared tagging solution is added to the gel containing protein under argon atmosphere. The reaction tube is standing for about 3 h at about 45° C. without shaking. After supernatant is discarded, the gel is washed with 50% acetonitrile/0.1% TFA (1 mL, x3), washed with 50% acetonitrile (1 mL), washed with acetonitrile (1 mL), and dried in vacuum.

EXAMPLE 3

In-Gel Digestion & Mass Analysis

Combined solution of 50 mM ammonium bicarbonate (45 μl) and trypsin (0.1 μg/μl, 6 μl) is added to the dried gel for digestion, and the solution is incubated for about 12 to 18 h at 37° C. The supernatant is collected by pipette, and peptides digested are extracted by 50% acetonitrile/0.1% trifluoroacetic acid (100 μl), and by acetonitrile (100 μl). The combined peptide solution is dried in vacuum.

The dried sample is dissolved in 20 uL of 0.1% TFA solution, and loaded onto a $C_{18}$ trap column prepared (I.D 250 mm, length 30 mm, particle size 5 μm) for desalting and concentration at a flow rate 20 μl/min. Then, the peptides trapped are separated with gradient elution condition, mixed on-line with the matrix solution (CHCA in 50% acetonitrile/ 0.1% trifluoroacetic acid), and loaded subsequently on sample plate for MALDI mass analysis. The eluting peptide solution can also be introduced directly to ESI mass spectrometer.

The invention claimed is:

1. A method for labeling a phosphorylated site of a phosphoprotein and identifying the labeled site of the resulting labeled protein, comprising the steps of:
   a) tagging said phosphoprotein retained in a polymeric gel matrix with an aqueous labeling reagent mixture, thereby labeling said phosphorylated site of said phosphoprotein with a labeling tag containing a guanidine moiety;
   b) hydrolyzing the labeled protein with an enzyme to afford digested peptides; and
   c) subjecting said hydrolyzed peptides to mass spectrometry.

2. The method of claim 1, wherein said polymeric gel matrix is a polymer capable of immobilizing the phosphonrotein.

3. The method of claim 1, wherein said polymeric gel matrix is polyacrylamide gel prepared from solutions containing 1% to 30% acrylamide.

4. The method of claim 1, wherein said labeling reagent mixture contains base, labeling tag, reducing agent, and/or metal catalyst.

5. The method of claim 4, wherein said base is inorganic base.

6. The method of claim 4, wherein said base is organic base.

7. The method of claim 4, wherein said labeling tag is selected from compounds having sulfhydryl functional group.

8. The method of claim 7, wherein said sulfhydryl functional group is prepared by reducing disulfide form of a labeling tag dimer with reducing agent.

9. The method of claim 8, wherein said reducing agent is selected from the group consisting of tris(2-cyanoethyl )phosphine (TCNEP), tris(2-carboxyethyl )phosphine (TCEP), tris(hydroxypropyl)phosphine (THPP), and tributylphosphine (TBP).

10. The method of claim 7, wherein said sulfhydryl functional group is prepared by deprotecting a protected sulfhydryl group through alkaline hydrolysis or nucleophilic displacement just before the tagging step.

11. The method of claim 4, wherein said labeling tag is guanidinoalkanethiol and/or an isomer thereof which is isotopically coded with an isotope and shows same chemical reactivity but different mass.

12. The method of claim 11, wherein said guanidinoalkanethiol is guanidinoethanethiol.

13. The method of claim 1, wherein said phosphorylated site is phosphoserine and/or phosphothreonine.

14. The method of claim 1, wherein said enzyme is a protease.

15. The method of claim 1, wherein said enzyme is selected from the group consisting of trypsin, endoproteinase Arg-C, and endoproteinase Lys-C.

16. The method of claim 1, wherein said digested peptides are quantified by mass spectrophotometry with or without separation by chromatography.

17. The method of claim 1,
wherein,
step (a) is performed by in-gel β-elimination of phosphate groups from phosphoproteins immobilized in a polymeric gel matrix, and in-gel Michael addition of a nucleophilic chemical tag having guanidine moiety, and the reagents, which is used for the in-gel Michael addition of a nucleophilic chemical tag having guanidine moiety, is selectively removed before step (b).

18. The method of claim 17, wherein said in-gel β-elimination of phosphate groups from phosphoproteins is carried out in a basic aqueous solotion.

19. The method of claim 17, wherein said polymeric gel matrix is polyacrylamide gel prepared by solution having 5% to 15% acrylamide.

20. The method of claim 17, wherein said nueleophilic chemical tag is guanidinoalkanethiol and/or an isomer thereof which is isotopically coded with an isotope and shows same chemical reactivity but different mass.

21. The method of claim 20, wherein said guanidinoalkanethiol is guanidinoethanethiol.

22. The method of claim 17, wherein said nueleophilic chemical tag is prepared during tagging reaction from disulfide form thereof.

23. The method of claim 17, wherein said phosphorylated site is phosphoserine and/or phosphothreonine.

* * * * *

SEQUENCE LISTING

```
<160> NUMBER OF SEQ ID NOS: 4

<210> SEQ ID NO 1
<211> LENGTH: 14
<212> TYPE: PRT
<213> ORGANISM: Artificial Sequence
<220> FEATURE:
<223> OTHER INFORMATION: GET-tagged peptide of alpha-casein
<220> FEATURE:
<221> NAME/KEY: SITE
<222> LOCATION: (10)..(10)
<223> OTHER INFORMATION: S denotes guanidinoethylcysteine site, formerly
      phosphoserine site.

<400> SEQUENCE: 1

Val Pro Gln Leu Glu Ile Val Pro Asn Ser Ala Glu Glu Arg
1               5                   10

<210> SEQ ID NO 2
<211> LENGTH: 12
<212> TYPE: PRT
<213> ORGANISM: Artificial Sequence
<220> FEATURE:
<223> OTHER INFORMATION: the peptide of alpha-casein
<220> FEATURE:
<221> NAME/KEY: SITE
<222> LOCATION: (1)..(1)
<223> OTHER INFORMATION: S denotes guanidinoethylcysteine site, formerly
      phosphoserine site.
<220> FEATURE:
<221> NAME/KEY: SITE
<222> LOCATION: (8)..(8)
<223> OTHER INFORMATION: S denotes guanidinoethylcysteine site, formerly
      phosphoserine site.

<400> SEQUENCE: 2
```

```
Ser Glu Glu Ile Val Pro Asn Ser Val Glu Gln Lys
1               5                   10

<210> SEQ ID NO 3
<211> LENGTH: 7
<212> TYPE: PRT
<213> ORGANISM: Artificial Sequence
<220> FEATURE:
<223> OTHER INFORMATION: the peptide of alpha-casein
<220> FEATURE:
<221> NAME/KEY: SITE
<222> LOCATION: (1)..(1)
<223> OTHER INFORMATION: S denotes guanidinoethylcysteine site, formerly
      phosphoserine site.

<400> SEQUENCE: 3

Ser Glu Glu Ser Ile Thr Arg
1               5

<210> SEQ ID NO 4
<211> LENGTH: 20
<212> TYPE: PRT
<213> ORGANISM: Escherichia coli
<220> FEATURE:
<221> NAME/KEY: SITE
<222> LOCATION: (20)..(20)
<223> OTHER INFORMATION: S denotes guanidinoethylcysteine site, formerly
      phosphoserine site.

<400> SEQUENCE: 4

Gly Phe Ser Gly Glu Asp Ala Thr Pro Ala Leu Glu Gly Ala Asp Val
1               5                   10                  15

Val Leu Ile Ser
            20
```